US009586878B2

(12) United States Patent
Yi et al.

(10) Patent No.: US 9,586,878 B2
(45) Date of Patent: Mar. 7, 2017

(54) METHOD FOR SYNTHESIZING A SUGAR ALCOHOL (71) Applicant: AGENCY FOR SCIENCE, TECHNOLOGY AND RESEARCH, Singapore (SG)

(72) Inventors: Guangshun Yi, Singapore (SG); Yugen Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/390,757

(22) PCT Filed: Apr. 5, 2013

(86) PCT No.: PCT/SG2013/000134
§ 371 (c)(1),
(2) Date: Oct. 3, 2014

(87) PCT Pub. No.: WO2013/151510
PCT Pub. Date: Oct. 10, 2013

(65) Prior Publication Data
US 2015/0057470 A1 Feb. 26, 2015

(30) Foreign Application Priority Data
Apr. 5, 2012 (SG) ................ 201202511-0

(51) Int. Cl.
C07C 29/14 (2006.01)
C07C 29/132 (2006.01)

(52) U.S. Cl.
CPC ................ *C07C 29/132* (2013.01)

(58) Field of Classification Search
CPC .................................. C07C 29/132
USPC ............................... 568/852, 863
See application file for complete search history.

(56) References Cited

U.S. PATENT DOCUMENTS

| 3,980,719 | A |   | 9/1976  | Buckl et al. |         |
|-----------|---|---|---------|--------------|---------|
| 5,516,960 | A | * | 5/1996  | Robinson     | 585/639 |
| 2010/0317901 | A1 | * | 12/2010 | Chaudhari et al. | 568/861 |

FOREIGN PATENT DOCUMENTS

| EP | 2 011 569 A1 | 1/2009 |
| JP | 2012-041335  | 3/2012 |

OTHER PUBLICATIONS

Kobayashi et al. Transfer hydrogenation of cellulose to sugar alcohols over supported ruthenium catalysts. Chemical Communications, 2011, vol. 47, 2366-2368.*
Palkovits et al. Hydrogenolysis of cellulose combining mineral acids and hydrogenation catalysts. Green Chemistry, 2010, vol. 12, 972-978.*
Yang et al. Recent Developments in the Catalytic Conversion of Cellulose into Valuable Chemicals. Chinese Journal of Catalysis, 2011, vol. 32 (5), 716-722.*
Alexander Emodi, "Xylitol — Its Properties and Food Applications", Food Technology, vol. 32, No. 1, pp. 28-32, (Jan. 1978).
PCT Notification of Transmittal of the International Search Report and the Written Opinion of the International Searching Authority, or The Declaration for PCT Counterpart Application No. PCT/SG2013/000134 Containing International Search Report, 13 pgs. (May 23, 2013).
PCT International Preliminary Report on Patentability for PCT Application No. PCT/SG2013/000134, 9 pgs. (Oct. 7, 2014).
J.J. Verandel, et al., "Catalytic one-pot production of smal organics from polysaccharides," Synthesis, vol. 11, pp. 1649-1677 (2011).
Yi Guangshun, et al., "One-pot selective conversion of hemiceiiulose (xylan) to xylitol under mild conditions," ChemSusChem, vol. 5, pp. 1383-1387 (2012).
Chen Luc. et al., "Cellulose Conversion into Polyois Catalyzed by Reversibly Formed Acids and Supported Ruthenium Clusters in Hot Water", Angenandte Chemie International Edition, vol. 46, No. 40, pp. 7638-7639 (2007).
Jan Geboers, et al., "Efficient catalytic conversion of concentrated cellulose feeds to hexitols with heteropoly acids and Ru on carbon", Chemical Communications, vol. 46, No. 20, pp. 3577-3579 (2010).
Extract from the Register of European Patents for counterpart EP patent application No. EP2834212, published Oct. 14, 2015. 2 pgs. (Database updated Jan. 16, 2016).
R.S. Prakasham, at al., "Current trends in biotechnological production of xyiitol and future prospects," Current Trends in Biotechnology and Pharmacy, vol. 3, Issue 1, pp. 8-36 (Jan. 2009).
Kauko K. Makinen, "The Rocky Road of Xylitol to its Clinical Application," Journal of Dental Research, vol. 79, Issue 6, pp. 1352-1355 (2000).
FDA. 21 CFR § 101.80, Code of Federal Regulations, 141-143 pgs. (Apr. 1, 2012).
JECFA Who food additives series No. 12. 7 pgs. (Apr. 18, 1977) http://www.inchem.org/docurnents/jecfa/jecmono/v12je22:htm.
Jun Seok Kim, et al., "Cellulose Hydrolysis Under Extremely Low Sulfuric Acid and High-Temperature Conditions," Applied Biochemistry and Biotechnology, vol. 91-93, pp. 331-340 (2001).
MMCD (2007) http://mmcd/nmrfam/wisc/edu/expnmr/expnmr_00131.html.
European Patent Office Communication enclosing Extended European Search Report for corresponding European Patent Application No. 13772792.1, 10 pp., (Sep. 16, 2015).
Database WPI, Week 201220, Accession No. 2012-C65876, Thomson Scientific, London, Great Britain, XP-002744089, 1 pg., (2012).
Hirokazu Kobayashi, et al., "Synthesis of Sugar Alcohols by Hydrolytic Hydrogenation of Cellulose Over Supported Metal Catalysts", Green Chemistry, vol. 13, No. 2, pp. 326-333, (Feb. 2011).
J. Wisniak, et al., "Hydrogenation of Xylose to Xylitol", Industrial & Engineering Chemistry Product Research and Development, vol. 13, No. 1, pp. 75-79, (1974).

(Continued)

*Primary Examiner* — Sikarl Witherspoon
(74) *Attorney, Agent, or Firm* — Blakely, Sokoloff, Taylor & Zafman LLP (57) ABSTRACT

A method for synthesizing a sugar alcohol comprising the step of hydrolyzing a polysaccharide in the presence of hydrogen ions ($H^+$), an alcoholic reducing agent and a hydrogen transfer catalyst to form the sugar alcohol.

20 Claims, 4 Drawing Sheets

(56) References Cited

OTHER PUBLICATIONS

K. K. Makinen, "Can the Pentitol-Hexitol Theory Explain the Clinical Observations Made with Xylitol?", Medical Hypotheses, vol. 54, No. 4, pp. 603-613, (2000).

Fran Gare, "Chapter 1—The Sweetener of Choice" and "Chapter 2—The Healing Effects of Xylitol", the Sweet Miracle of Xylitol, Basic Health Publications, Inc., Laguna Beach, CA, 38 pp. (including cover page, copyright page, table of contents, and chapters 1 and 2), (2003).

* cited by examiner

METHOD FOR SYNTHESIZING A SUGAR ALCOHOL

CROSS-REFERENCE TO RELATED APPLICATIONS

This patent application is a U.S. National Phase Application under 35 U.S.C. §371 of International Application No. PCT/SG2013/000134, filed Apr. 5, 2013, entitled A METHOD FOR SYNTHESIZING A SUGAR ALCOHOL, which claims priority to Singapore Patent Application No. 201202511-0, filed Apr. 5, 2012.

TECHNICAL FIELD

The present invention generally relates to a method for synthesizing a sugar alcohol. The present invention relates to a method for synthesizing at least one of xylitol, mannitol and sorbitol.

BACKGROUND

Two polysaccharides, cellulose and hemicellulose, make up approximately 70% to 85% of lignocellulose, one which in turn makes up the vast majority of woody biomass and agricultural residues.

One particular derivative obtainable from these polysaccharides is xylitol, a five-carbon sugar alcohol, which has several applications and potential use in some industries that may include food, odontological and pharmaceutical.

Industrially, xylitol may be produced from the reduction of pure xylose via acid hydrolysis of xylan containing products such as hardwoods or corn cobs. Such a process contains multiple steps, which may include production of xylose by an initial acid decomposition of xylan containing natural products; concentrating the hydrolysis solution to remove impurities; catalytic hydrogenation of xylose to xylitol under high pressure hydrogen gas (up to 50 atm) at elevated temperatures (commonly above 160° C.); and then purification and isolation of the xylitol. This multi-step process is laborious, costly, energy intensive and environmental unfriendly. Moreover, the yield of xylitol attained is only 50% to 60% of the xylan present in the raw materials. In addition, due to the use of the high pressure hydrogen gas, sophisticated hydrogenation facilities are required which safety is a major concern.

Xylitol may also be synthesized by other similar multi-step processes with modifications made to some of the steps within, such as using basic hydrolysis or enzymatic hydrolysis instead of acidic components etc.

Other modifications may include the use of xylitol producing microbial strains in the fermentation of xylose from crude hydrolysate to xylitol. However, such bioconversion suffers from lackluster yields due to the presence of microbial growth inhibitors that are generated from upstream degradation of cellulose or hemicellulose via chemical (acid or base) hydrolysis. Microbial toxicity is also associated with fermentation variables such as microbial physiological growth conditions, dissolved oxygen concentration and pH of the medium. In general, biomass hydrolysate inhibitors comprising sugar or lignin degradation products, derived from lignocellulosic structure, and heavy metal ions remain a serious drawback for using bio-processes.

Accordingly, there is a need for a more effective production process of a sugar alcohol such as xylitol that ameliorates the above limitations.

There is a need for the reduction of steps in the above process that overcomes, or at least ameliorates, one or more of the disadvantages described above.

SUMMARY

According to a first aspect, there is provided a method for synthesizing a sugar alcohol comprising the step of hydrolyzing a polysaccharide in the presence of hydrogen ions ($H^+$), an alcoholic reducing agent and a hydrogen transfer catalyst to form the sugar alcohol.

Advantageously, the method may be a "one-pot" method to synthesize the sugar alcohol. The method may take place in a reaction zone. The polysaccharide may be hydrolyzed to a monosaccharide, which then undergoes reduction to form the sugar alcohol. The method may optionally exclude the step of isolating a monosaccharide intermediate from the reaction. Hence, the method may be a straight forward method as compared to conventional methods which require numerous steps of hydrolyzing the polysaccharide to form a monosaccharide, isolating the monosaccharide and then reducing the monosaccharide in the presence of hydrogen gas to form the corresponding sugar alcohol(s).

Advantageously, the sugar alcohol may be synthesized at a high yield from the polysaccharide.

Advantageously, due to the low boiling point of the alcoholic reducing agent, the remaining alcoholic reducing agent can be easily evaporated from the reaction at the end of the reaction to aid in the extraction of the sugar alcohol. The alcoholic reducing agent may also be recycled without substantially affecting the yield of the sugar alcohol.

Advantageously, the pH of the reaction may be in the range of about 2 to about 3, such that special equipment such as high nickel alloy equipment may not be necessary.

Advantageously, the method may selectively convert a desired polysaccharide from a mixture of two or more polysaccharides to the corresponding sugar alcohol. The method may be a one-pot method to convert a mixture of polysaccharides to their corresponding sugar alcohols by adjusting the reaction conditions to thereby selectively convert a desired polysaccharide to its corresponding sugar alcohol(s).

The method for synthesizing a sugar alcohol may be undertaken in a reaction zone.

In one embodiment, there is provided a method for synthesizing xylitol comprising the step of hydrolyzing hemicellulose in the presence of hydrogen ions ($H^+$), an alcoholic reducing agent and a hydrogen transfer catalyst to form the xylitol.

The method for synthesizing xylitol may comprise the step of reacting a mixture comprising hemicellulose, a sulphuric acid solution and an alcoholic reducing agent in the presence of a transition metal catalyst in a reaction zone under conditions to thereby form the xylitol.

According to a second aspect, there is provided a method of synthesizing a plurality of sugar alcohols from a mixture of hemicellulose and cellulose, the method comprising the steps of (a) hydrolyzing said hemicellulose in the presence of hydrogen ions ($H^+$), an alcoholic reducing agent and a hydrogen transfer catalyst to form xylitol; and (b) hydrolyzing said cellulose in the presence of said hydrogen ions ($H^+$), said alcoholic reducing agent and said hydrogen transfer catalyst to form at least one of sorbitol and mannitol.

DEFINITIONS

The following words and terms used herein shall have the meaning indicated:

The term "one-pot", when referring to a method, may be interpreted broadly to refer to a multi-step chemical reaction that is carried out in a reaction zone without any isolation of the intermediate (or of any impurities). Hence, the reactants may be simultaneously or successively added to the reaction zone and the final products can be extracted from the reaction zone without the need to intentionally stop the reaction in order to extract the intermediate or any impurities that may be formed as by-products from the first step chemical reaction. In this one-pot method, the intermediate is generated in the first step chemical reaction and the intermediate is then reacted in situ with the other component(s) present in or introduced into the same reaction zone to form the final product(s).

The term "reaction zone" is to be interpreted broadly to refer to a controlled environment in which a reaction is taking place. For the "one-pot" method, the reactants are introduced into a reaction zone and the desired products are extracted from the same reaction zone. A reaction zone can be, for example, a reactor or a section of a reactor in which the reaction conditions can be controlled. Typically, the reaction zone is a reactor. The term "reactor" then refers to an apparatus in which the reaction zone is present.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5 of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a method for synthesizing a sugar alcohol will now be disclosed.

The method for synthesizing a sugar alcohol may comprise the step of hydrolyzing a polysaccharide in the presence of hydrogen ions ($H^+$), an alcoholic reducing agent and a hydrogen transfer catalyst to form the sugar alcohol.

The method may be undertaken in a reaction zone. Hence, the method may be considered as a "one-pot" method.

The polysaccharide, hydrogen ions, alcoholic reducing agent and hydrogen transfer catalyst may be introduced into the reaction zone at the same time or at different times. The polysaccharide, hydrogen ions, alcoholic reducing agent and hydrogen transfer catalyst may be replenished when necessary.

The polysaccharide may comprise hemicellulose, cellulose or a combination thereof. The polysaccharide may be utilized in the form of a dried ground material or in the form of an aqueous extract.

The polysaccharide may be obtained from or extracted from a plant source that is not particularly limited and can include oats (for example oat hulls), bagasse (for example sugarcane bagasse), maize (for example corn cobs and stalks), coconut (for example coconut husks), poplar, birch wood, alder, beechwood (for example beechwood shavings), almond shells, straw, cotton seed hulls, etc. The polysaccharide may be obtained from wood-chemical industries.

The hydrogen ions may be sourced from an acid. Water may be added so as to form an acidic solution. The acid may exclude acids having a halide anion. The acid may exclude acids having a chlorine anion. The acid, may be a diprotic acid. The acid may be a sulphur oxoacid. The sulphur oxoacid may be selected from sulphuric acid and sulphurous acid.

The acid may be present at a mol % $H^+$ in the range of about 45 mol % $H^+$ to about 55 mol % $H^+$, about 45 mol % $H^+$ to about 50 mol % $H^+$, about 50 mol % $H^+$ to about 55 mol % $H^+$, or about 49 mol % $H^+$ to about 50 mol % $H^+$. In one embodiment, the amount of acid present may be about 49.2 mol % $H^+$.

The acid may be present at a weight percentage in the range of about 0.1% w/w to about 0.2% w/w, about 0.1% w/w to about 0.15% w/w, about 0.15% w/w to about 0.2% w/w, about 0.16% w/w to about 0.18% w/w, based on the weight of solvent. In one embodiment, the weight percentage of the acid is about 0.17% w/w based on the weight of solvent.

The alcoholic reducing agent may be an aliphatic alcohol. The aliphatic alcohol may be a primary alcohol or secondary alcohol. The primary alcohol may have 2 to 10 carbon atoms. The primary alcohol may be selected from the group consisting of ethanol, n-propanol, n-butanol, iso-butanol, n-pentanol, 2-methyl-1-butanol, isopentanol, neopentanol, n-hexanol, 2-methyl-1-pentanol, 4-methyl-1-pentanol, 3-methyl-1-pentanol, n-heptanol, n-octanol, n-nonanol and n-decanol.

The secondary alcohol may have 3 to 10 carbon atoms. The secondary alcohol may be selected from the group consisting of iso-propanol, sec-butanol, 2-pentanol, 3-pentanol, 3-methyl-2-butanol, neopentanol, 2-hexanol, 3-hexanol, 2-methyl-3-pentanol, 4-methyl-2-pentanol, 3-methyl-2-pentanol, 2-heptanol, 3-heptanol, 2-octanol, 2-nanonol and 2-decanol. The alcoholic reducing agent may be isopropanol.

Due to the low boiling point of some of the alcoholic reducing agents (as compared to that of water), the alcoholic reducing agent may be evaporated easily so as to allow for the sugar alcohol product to be extracted easily from the reaction.

The remaining alcoholic reducing agent may be recycled and reused without any significant detrimental effect on the yield of the sugar alcohol.

The water (making up the acidic solution) and the alcoholic reducing agent may be present at a volumetric ratio in the range of about 10:1 to about 1:10, about 7:1 to about 1:7, about 3:1 to about 1:3. The volumetric ratio may be about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

The catalyst may be a transition metal catalyst. The transition metal catalyst may be a transition metal hydride or a transition metal halide. The catalyst may be ruthenium hydride or ruthenium halide. The catalyst may be selected from the group consisting of $RuCl_2(PPh_3)_3$, $RuH_2(PPh_3)_3$, $RuH_2(PPh_3)_4$, $RuH(OAc)(PPh_3)_3$, $Ru(OAc)_2(PPh_3)_3$(p-cymene)Ru(dpen)Cl, and $Cp*Ru(OMe)_2$. The ruthenium catalyst may be provided on a support selected from the group consisting of active carbon, titania, γ-alumina, and cerium oxide. The catalyst may be ruthenium metal nanoparticles on carbon support (or Ru/C).

The amount of catalyst used may be in the range of about 2 mol % to about 2.5 mol %, about 2.5 mol % to about 3 mol %, or about 2.3 mol % to about 2.5 mol %. In one embodiment, the amount of catalyst may be about 2.4 mol %.

The catalyst may be recycled and reused. The catalyst may be used for at least 2 times, at least 3 times, at least 4 times, at least 5 times, or at least 6 times, without any significant detrimental effect on the sugar alcohol yield.

The method may be undertaken at a reaction temperature selected from the range of about 135° C. to about 155° C., about 135° C. to about 140° C., about 135° C. to about 145° C., about 135° C. to about 150° C., about 140° C. to about 155° C., about 145° C. to about 155° C., or about 150° C. to about 155° C. The reaction temperature may be about 140° C. or about 150° C.

The method may be undertaken for a time period selected from the range of about 2.5 hours to about 8.5 hours, about 2.5 hours to about 3.5 hours, about 2.5 hours to about 4.5 hours, about 2.5 hours to about 5.5 hours, about 2.5 hours to about 6.5 hours, about 2.5 hours to about 7.5 hours, about 2.5 hours to about 8.5 hours, about 3.5 hours to about 8.5 hours, about 4.5 hours to about 8.5 hours, about 5.5 hours to about 8.5 hours, about 6.5 hours to about 8.5 hours, about 7.5 hours to about 8.5 hours, about 3 hours to about 4 hours, about 4 hours to about 5 hours, about 5 hours to about 6 hours, about 6 hours to about 7 hours, or about 7 hours to about 8 hours. The reaction time period may be about 3 hours, 4 hours, 5, hours, 6 hours, 7 hours, or 8 hours.

The sugar alcohol may be selected from the group consisting of xylitol, mannitol and sorbitol.

The yield of the sugar alcohol may be greater than about 60%, greater than about 65%, greater than about 70%, greater than about 75%, greater than about 80%, greater than about 85%, greater than about 90%, or greater than about 95%.

Where the sugar alcohol to be synthesized is xylitol, the polysaccharide comprises xylan-containing hemicellulose, which is the starting material for the synthesis of xylitol. Here, xylan is firstly hydrolyzed into xylose with a catalytic amount of the acidic solution. Following that, xylose is reduced to xylitol by the alcoholic reducing agent in the presence of the hydrogen transfer catalyst. The reaction scheme is shown in Scheme 1 in which the alcoholic reducing agent used is isopropanol and the hydrogen transfer catalyst is active carbon supported ruthenium.

Scheme 1

Hemicellulose (xylan)

Xylose → Xylitol

As shown in Scheme 1, isopropanol is converted to acetone. The inventors have found that during this hydrogen transfer process, about 1 mol % to about 2 mol % of isopropanol is converted to acetone, while still achieving high yields of xylitol (above 75%). This indicates the high hydrogen transfer efficiency of the isopropanol in the above reaction.

In one embodiment, there is provided a method for synthesizing xylitol, comprising the step of reacting a reaction mixture comprising a polysaccharide, hydrogen ions ($H^+$) and an alcoholic reducing agent in the presence of a hydrogen transfer catalyst under conditions to thereby form said xylitol. The method may be undertaking in a reaction zone.

The method for synthesizing xylitol may comprise the step of reacting a reaction mixture comprising a hemicellulose feedstock, a sulphuric acid solution and an alcoholic reducing agent in the presence of a transition metal catalyst in a reaction zone under conditions to thereby form the xylitol.

The method of synthesizing the sugar alcohol such as xylitol may be a one-pot method in which it may not be necessary to remove the xylose intermediate from the reaction zone. Hence, the method of synthesizing xylitol may optionally exclude a step of isolating a xylose intermediate. The xylose intermediate may react in situ to form the final xylitol product.

In embodiments where the polysaccharide is present as mixture of hemicellulose and cellulose, the hemicellulose may be selectively converted to the corresponding sugar alcohol (xylitol) over cellulose. The cellulose may remain unreacted. In order to convert the cellulose to the corresponding sugar alcohols or mannitol and/or sorbitol, the same reactants may be used but at different reaction conditions (such as a higher reaction temperature and/or reaction time).

There may be provided a method of synthesizing a plurality of sugar alcohols from a mixture of hemicellulose and cellulose, the method comprising the steps of (a) hydrolyzing said hemicellulose in the presence of hydrogen ions ($H^+$), an alcoholic reducing agent and a hydrogen transfer catalyst to form xylitol; and (b) hydrolyzing said cellulose in the presence of said hydrogen ions ($H^+$), said alcoholic reducing agent and said hydrogen transfer catalyst to form at least one of sorbitol and mannitol.

The method of synthesizing a plurality of sugar alcohols may be undertaking in a reaction zone. The mixture of hemicellulose and cellulose may additionally include lignin, which remains unreacted during the method and which can be extracted after step (a). The lignin may be extracted into the alcohol/water phase and precipitated as the alcohol evaporates.

In hydrolyzing step (a), the acidic solution may catalyze the hydrolysis of the xylan present in the polysaccharide feedstock to xylose intermediate while the xylose intermediate is reduced to xylitol due to the transfer of hydrogen from the alcoholic reducing agent in the presence of the catalyst. This takes place in the reaction zone. The reaction conditions for this step (a) may include a temperature in the range of about 135° C. to about 155° C. for about 2.5 hours to about 8.5 hours.

Following which, if any lignin is present, the lignin may be extracted from the reaction zone.

In hydrolyzing step (b), additional amounts of the acidic solution and alcoholic reducing agent may be added to the same reaction zone as step (a) in order to convert the cellulose to mannitol and/or sorbitol. The reaction conditions for this step (b) may include a temperature in the range of about 240° C. to about 250° C. for about 11 hours to about 13 hours.

The temperature in step (b) may be selected from the range of about 240° C. to about 250° C., about 240° C. to about 245° C., or about 245° C. to about 250° C. The temperature may be about 245° C.

The time period in step (b) may be selected from the range of about 11 hours to about 13 hours, about 11 hours to about 12 hours, or about 12 hours to about 13 hours. The reaction time period may be about 12 hours.

In hydrolyzing step (b), the hydrogen ions ($H^+$) may be sourced from an acid in a water solvent. The acid may be present at a mol % $H^+$ in the range of about 45 mol % $H^+$ to about 55 mol % $H^+$, about 45 mol % $H^+$ to about 50 mol % $H^+$, about 50 mol % $H^+$ to about 55 mol % $H^+$, or about 49 mol % $H^+$ to about 50 mol % $H^+$. In one embodiment, the amount of acid present may be about 49.2 mol % $H^+$.

The acid may be present at a weight percentage in the range of about 0.1% w/w to about 0.2% w/w, about 0.1% w/w to about 0.15% w/w, about 0.15% w/w to about 0.2% w/w, about 0.16% w/w to about 0.18% w/w, based on the weight of solvent. In one embodiment, the weight percentage of the acid is about 0.17% w/w based on the weight of solvent.

The water (making up the acidic solution) and the alcoholic reducing agent may be present at a volumetric ratio in the range of about 10:1 to about 1:10, about 7:1 to about 1:7, about 3:1 to about 1:3. The volumetric ratio may be about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

The amount of hydrogen transfer catalyst used may be in the range of about 2 mol % to about 2.5 mol %, about 2.5% to about 3 mol %, or about 2.3 mol % to about 2.5 mol %. In one embodiment, the amount of catalyst may be about 2.4 mol %.

As such, it is possible to synthesize a plurality of sugar alcohols from a mixture of hemicellulose and cellulose in a one-pot reaction.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Non-limiting examples of the invention and a comparative example will be further described in greater detail by reference to specific Examples, which should not be construed as in any way limiting the scope of the invention.

Materials

Hemicellulose (Beechwood xylan, 96.6% purity, containing 6.46% wt % physisorbed water) was purchased from Sigma-Aldrich (of Missouri of the United States of America). The hemicellulose was used directly without any pre-treatment. D-Xylose (P99%), xylitol (99%), Ru/C (5 wt % metal), Amberlyst-15 resin and cellulose were purchased from Sigma-Aldrich. Iso-propanol (HPLC grade) was purchased from J. T. Baker (Avantor Performance Materials of Pennsylvania of the United States of America). Sulfuric acid (95-97%), hydrochloric acid (37%), Pd/C and Pd/C were purchased from Merck KGaA of Germany.

Product Analysis

After reaction, the reaction mixture was separated by filtration. The remaining solid (Ru/C catalyst and any unreacted hemicellulose) was washed with water, dried and weighed. Xylitol yield was analyzed using a Sugar Analyzer (DKK-TOA Corporation, Japan. Model: SU-300) and confirmed with isolation yield. The Sugar Analyzer was operated in sugar alcohol mode, with xylitol standard solution for calibration. Testing conditions: mobile phase: 200 mM NaOH, 0.5 mL min$^{-1}$, 39.9° C.

Xylitol Yield Calculation

The amount of converted xylitol was directly obtained from the results of the Sugar Analyzer. The yield was calculated by dividing the weight of xylitol obtained by the theoretical yield of xylitol. Theoretically, 75 mg hemicellulose can produce 78.04 mg xylitol by calculation.

The conversion of hemicellulose (or xylan) was obtained by calculating the mass difference of the hemicellulose (xylan) before and after reaction.

Characterization

Figure 1A:
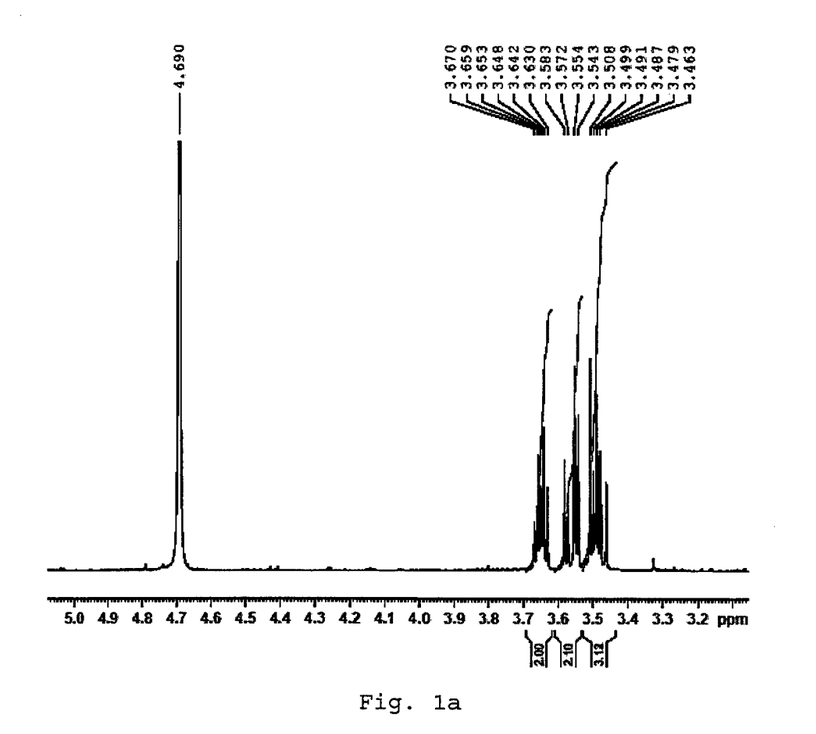
FIG. 1a is a $^1H$ Nuclear Magnetic Resonance (NMR) spectrum of the xylitol product.
Figure 1B:
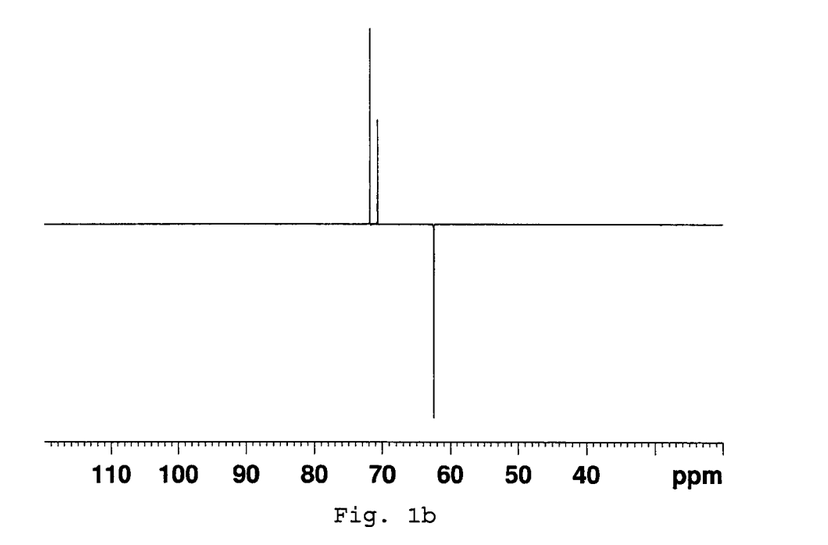
FIG. 1b is a $^{13}C$ NMR spectrum of the xylitol product.

The xylitol product was characterized by $^1$H and $^{13}$C nuclear magnetic resonance (NMR, Bruker AV-400 from Bruker Corporation of Massachusetts of the United States of America). FIG. 1a is the $^1$H NMR spectrum of xylitol while FIG. 1b is the $^{13}$C spectrum of xylitol. These spectra are quite consistent with the reference (obtained from the Madison Metabolomics Consortium Database (MMCD) for xylitol).

The Ru/C catalyst was characterized by transmission electron microscopy (FEI Tecnai F20 from FEI of Oregon of the United States of America).

Example 1

Temperature Effects

The effects of temperature on the synthesis of xylitol were investigated. 75 mg hemicellulose (67.77 mg hereafter, after deducting the physisorbed water and impurities, 0.513 mmol D-xylose units), 25 mg Ru/C (2.4 mol %), 4 ml water, 4 ml iso-propanol, 7 µl H$_2$SO$_4$ (0.126 mmol, 49.2 mol % H$^+$) were mixed together in a 10 ml Teflon-lined hydrothermal reactor and allowed to react for 14 hours at varying temperatures of 100° C., 120° C., 130° C., 140° C., 150° C. and 160° C. The reactor was heated to the test temperature using a silicon oil bath or an oven and maintained at the test temperature for 14 hours with magnetic stirring at 600 rpm. After the reaction, the reactor was naturally cooled down.

Table 1 shows the results obtained from this example.

TABLE 1

Reaction temperature effect on the xylitol yield

| Entry | Temperature (° C.) | Xylitol (mg) | Yield (%) | Conversion (%) |
|---|---|---|---|---|
| 1 | 100 | 8.58 | 10.99% | 48.8% |
| 2 | 120 | 34.6 | 44.34% | 96.4% |
| 3 | 130 | 46.6 | 59.71% | 98.5% |
| 4 | 140 | 62.8 | 80.47% | 98.3% |
| 5 | 150 | 62.6 | 80.22% | 93.6% |
| 6 | 160 | 58.6 | 75.09% | 95.5% |

Figure 2:
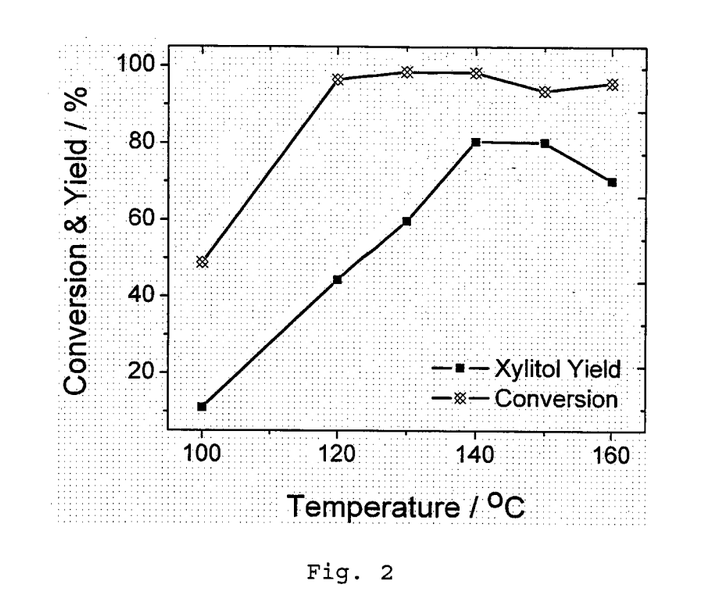
FIG. 2 is a graph showing the production yield of xylitol as a result of the reaction temperature.

It was found that in the temperature range of 100° C. to 140° C., the yield of xylitol increased almost linearly, as shown in FIG. 2. The higher the reaction temperature, the higher the xylitol yield obtained. At 140° C. and 150° C., the xylitol yield reached the highest.

In addition, an increase in the reaction temperature led to an increase in the hemicellulose conversion (see Table 1). This indicated that a higher temperature is favored for the hydrolysis of hemicellulose. When the temperature was lower than 140° C., it was difficult to digest the hemicellulose. The hemicellulose was only digested when the temperature was equal to or above 140° C. When the reaction temperature was higher than 150° C., the xylitol yield decreased. Hence, the reaction temperature was fixed at 140° C. for the following experiments.

Example 2

Reaction Time Effects

The effects of reaction time on the synthesis of xylitol were investigated. 67.77 mg hemicellulose (0.513 D-xylose unit), 25 mg Ru/C (2.4 mol %), 4 ml water, 4 ml iso-propanol and 7 µl H$_2$SO$_4$ were mixed in a 10 ml Teflon-lined hydrothermal reactor and reacted at a temperature of 140° C. at varying reaction time periods of 1 hour, 2 hours, 3 hours, 4 hours, 5 hours, 6 hours, 8 hours, 10 hours, 12 hours and 14 hours. The reactor was heated to 140° C. using a silicon oil bath or an oven and maintained at this temperature for the test time period with magnetic stirring at 600 rpm. After the reaction, the reactor was naturally cooled down.

Figure 3:
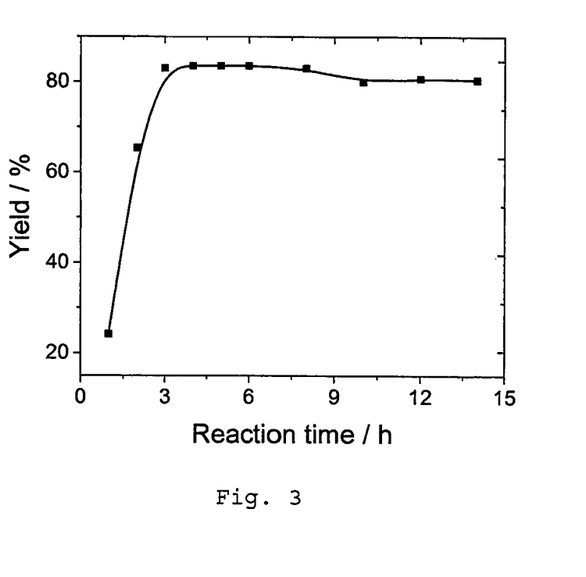
FIG. 3 is a graph showing the production yield of xylitol as a result of the reaction time.

FIG. 3 shows the production yield of xylitol with respect to the reaction time at a temperature of 140° C. Referring to FIG. 3, it can be observed that the reaction was almost completed in 3 hours, with a high xylitol yield of more than 83%. Similar xylitol yields were obtained as the reaction progressed from 3 hours to 8 hours. If the reaction time was longer than 8 hours, the xylitol yield slightly decreased. Hence, the reaction time was fixed at 3 hours for the following experiments.

Example 3

Solvent Effects

In this reaction system, a mixture of water and iso-propanol was used as the solvent. Water is required to hydrolyze hemicellulose to the D-xylose monomer while iso-propanol acts as a hydrogen source in the presence of Ru/C catalyst to transfer hydrogen to xylose in order to reduce xylose to xylitol.

Here, the effects of the water to iso-propanol ratio on the synthesis of xylitol were investigated. 67.77 mg hemicellulose (0.513 mmol D-xylose unit), 25 mg Ru/C (2.4 mol %), varying amounts of water, varying amounts of iso-propanol and 7 µl H$_2$SO$_4$ were mixed in a 10 ml Teflon-lined hydrothermal reactor and reacted at a temperature of 140° C. for 3 hours. Total reaction volume was fixed at about 8 ml. The reactor was heated to 140° C. using a silicon oil bath or an oven and maintained at this temperature for 3 hours with magnetic stirring at 600 rpm. After the reaction, the reactor was naturally cooled down.

Table 2 shows the results obtained from this example.

TABLE 2

Solvent ratio effect on the xylitol yield

| Entry | Water (ml) | Iso-propanol (ml) | Ratio | Xylitol (mg) | Xylan conversion (%) |
|---|---|---|---|---|---|
| 1 | 8 | 0 | — | 8.62 | 11.05 |
| 2 | 7 | 1 | 7:1 | 61.4 | 78.68 |
| 3 | 6 | 2 | 3:1 | 62.8 | 80.47 |
| 4 | 4 | 4 | 1:1 | 64.8 | 83.03 |
| 5 | 2 | 6 | 1:3 | 62.8 | 80.47 |
| 6 | 1 | 7 | 1:7 | 46.8 | 59.97 |
| 7 | 0 | 8 | — | 9.84 | 12.61 |

As shown in Table 2, in the case of only water or iso-propanol as solvent, only small amounts of xylitol was detected. However, when a mixture of water and iso-propanol was used as the solvent, the yield of xylitol significantly increased. From Table 2, when the ratio of water to iso-propanol was in the range from 7:1 to 1:3, no significant change in the xylitol yield was observed. This offers the flexibility to change the solvent compositions, especially for large-scale production. This is evident in an experiment carried out on a larger scale (in a 50 mL Teflon-lined hydrothermal reactor) in which 375 mg hemicellulose was used as the starting product and mixed with 125 mg of Ru/C (2.4 mol %), 20 ml water, 20 ml iso-propanol and 35 μl $H_2SO_4$ (that is, 5× scale up). Here, 313.3 mg of isolated xylitol (80.3% yield) was obtained, showing that the process can be scaled up effectively.

Compared with water, iso-propanol has a lower boiling point and can be easily evaporated during extraction of the xylitol from solution. The iso-propanol vapor can be condensed and recycled. A reaction based on 67.77 mg hemicellulose (0.513 mmol D-xylose unit), 25 mg Ru/C (2.4 mol %), 4 ml water, 4 ml recycled iso-propanol and 7 μl $H_2SO_4$ in a 10 ml Teflon-lined hydrothermal reactor at 140° C. for 3 hours did not have any significant detrimental effect on the product yield as 81.8% xylitol yield was obtained. Hence, the iso-propanol can be recycled for subsequent processes without significantly affecting the product yield.

Example 4

Amounts of Sulphuric Acid Used

Here, the effects of the amounts of sulphuric acid in the reaction mixture on the synthesis of xylitol were investigated. 67.77 mg hemicellulose (0.513 mmol D-xylose unit), 25 mg Ru/C (2.4 mol %), 4 ml water, 4 ml iso-propanol and varying amounts of $H_2SO_4$ (0 μl, 1 μl, 2 μl, 3 μl, 4 μl, 5 μl, 6 μl, 7 μl, 8 μl, 9 μl, 14 μl, 21 μl and 28 μl $H_2SO_4$) were mixed in a 10 ml Teflon-lined hydrothermal reactor and reacted at a temperature of 140° C. for 3 hours. The reactor was heated to 140° C. using a silicon oil bath or an oven and maintained at this temperature for 3 hours with magnetic stirring at 600 rpm. After the reaction, the reactor was naturally cooled down.

Figure 4:
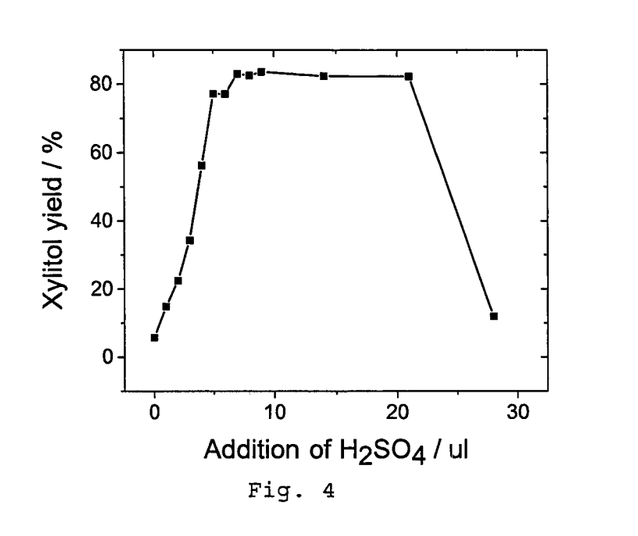
FIG. 4 is a graph showing the production yield of xylitol as a result of the amount of $H_2SO_4$ added.

FIG. 4 shows the production yield of xylitol as a result of the amount of $H_2SO_4$ added. From FIG. 4 and Table 3 (See Example 5 below), it can be observed that without any acid, the xylitol yield was only 5.71%. However, when small amounts of $H_2SO_4$ were added, the xylitol yield significantly increased. When 7 μl 96% $H_2SO_4$ (equal to 0.17% w/w, 49.2 mol % $H^+$) was added, the xylitol yield reached the highest, as shown in FIG. 4. However, addition of $H_2SO_4$ in excess of 21 μl led to a decrease in the xylitol yield. Hence, the amount of $H_2SO_4$ was fixed at 7 μl.

The optimized conditions with 7 μl of 96% $H_2SO_4$ in 8 mL of mixture solvent (pH~2) for the reaction at 140° C. was comparable to the extremely low acid (ELA) conditions (a system with pH 2.2, for reaction at more than 200° C.) defined by the National Renewable Energy Laboratory (NREL, of the United States of America). Since the corrosive characteristics of ELA are close to those of neutral aqueous reactions, standard-grade stainless steel equipment can be used instead of high-nickel alloys. As such, the use of ELA can be considered as a green technology. In the present example, since the corrosion capability of the 7 μl 96% $H_2SO_4$ solution is similar to that of ELA (pH 2 as compared to pH 2.2 of the ELA) and the reaction temperature of 140° C. is much lower than that used by the NREL, the reaction mixture used herein can also be used with standard-grade stainless steel equipment, which is promising for plant scale production.

Example 5

Types of Acid Used

Here, the effects of different types of acid on the synthesis of xylitol were investigated. 67.77 mg hemicellulose (0.513 mmol D-xylose unit), 25 mg Ru/C (2.4 mol %), 4 ml water, 4 ml iso-propanol and 49.2 mol % of $H^+$ were mixed in a 10 ml Teflon-lined hydrothermal reactor and reacted at a temperature of 140° C. for 3 hours. The various acids tested were $H_2SO_4$, HCl, Amberlyst-15 (at varying amounts) and sulfonated carbon. The reactor was heated to 140° C. using a silicon oil bath or an oven and maintained at this temperature for 3 hours with magnetic stirring at 600 rpm. After the reaction, the reactor was naturally cooled down. Table 3 shows the results obtained from this example.

TABLE 3

Type of acid on the yield of xylitol

| | No acid | $H_2SO_4$ | HCl | Amberlyst-15 | Amberlyst-15[a] | Amberlyst-15[b] | Sulfonated carbon |
|---|---|---|---|---|---|---|---|
| Xylitol (mg) | 4.46 | 64.8 | 4.46 | 28.2 | 37.4 | 11.2 | 2.24 |
| Xylitol yields (%) | 5.71% | 83.03% | 5.71% | 36.14% | 47.92% | 14.35% | 2.87 |

[a]double amount of acid.
[b]four times of acid.

When an equivalent amount of HCl was used to replace sulfuric acid, negligible amount of xylitol was detected, in which the amount of xylitol detected was similar to that obtained in the control without any acid. Instead, high yield of xylose was detected (data not shown). It is obvious that hemicellulose had been hydrolyzed into xylose, but under HCl conditions, none of the xylose intermediate was converted to xylitol. This may be due to the existence of the Cl⁻ ion that quenched the activity of Ru/C catalyst in the transfer hydrogenation step from the xylose intermediate to xylitol.

When sulfuric acid was used, almost all of the xylose intermediate was converted to xylitol.

An equivalent amount of solid acid, Abmerlyst-15, was also tested to result in a xylitol yield of 36.14%. When the amount of Amberlyst-15 was doubled, the yield reached 47.92%. Further increase in the amount of this acid led to a decrease in the xylitol yield to 14.35%, as shown in Table 3 above.

When sulfonated carbon was used, the xylitol yield was lower than that of the control, indicating that sulfonated carbon is not as good as sulphuric acid

Example 6

Amounts of Catalyst Used

Here, the effects of different amounts of the Ru/C catalyst on the synthesis of xylitol were investigated. 67.77 mg hemicellulose (0.513 mmol D-xylose unit), varying amounts of Ru/C (2.4 mol %), 4 ml water, 4 ml iso-propanol and 7 μl $H_2SO_4$ were mixed in a 10 ml Teflon-lined hydrothermal reactor and reacted at a temperature of 140° C. for 3 hours. The reactor was heated to 140° C. using a silicon oil bath or an oven and maintained at this temperature for 3 hours with magnetic stirring at 600 rpm. After the reaction, the reactor was naturally cooled down. Table 4 shows the results obtained from this example.

When no catalyst was used, negligible amount of xylitol was detected, and instead, xylose was observed (data not shown). This suggested that the hemicellulose was hydrolyzed to xylose, but the xylose was not further converted to xylitol.

When the catalyst loading was increased, the xylitol yield increased steadily. The xylitol yield reached a maximum at a catalyst loading of 15 mg. Further increase to the catalyst amount to 20 mg and 25 mg only resulted in a slight increase in the xylitol yield.

TABLE 4

Amount of Ru/C catalyst on the yield of xylitol

| Ru/C (mg) | 0 | 5 | 10 | 15 | 20 | 25 |
|---|---|---|---|---|---|---|
| Xylitol (mg) | 1.82 | 21 | 33.6 | 64 | 64.2 | 64.8 |
| Yield | 2.33% | 26.91% | 43.55% | 82.01% | 82.27% | 83.03% |

Example 7

Recycling of Ru/C Catalyst

To test the durability of the Ru/C catalyst, the catalyst was recovered by centrifugation after the first reaction. The recovered catalyst was then directly used in the next few experiments. For all experiments, 67.77 mg hemicellulose (0.513 mmol D-xylose unit), 25 mg of Ru/C (2.4 mol %), 4 ml water, 4 ml iso-propanol and 7 μl $H_2SO_4$ were mixed in a 10 ml Teflon-lined hydrothermal reactor and reacted at a temperature of 140° C. for 3 hours. The reactor was heated to 140° C. using a silicon oil bath or an oven and maintained at this temperature for 3 hours with magnetic stirring at 600 rpm. After the reaction, the reactor was naturally cooled down.

Figure 5:
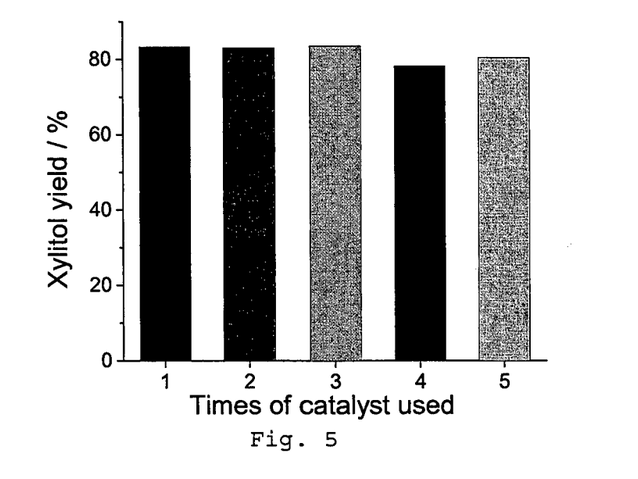
FIG. 5 is a bar graph showing the durability of Ru/C catalyst on the xylitol yields.

The results of this example are shown in FIG. 5. Referring to FIG. 5, the Ru/C catalyst demonstrated excellent recyclability in this reaction. There was no significant deactivation observed even when the catalyst was used for 5 runs since the xylitol yield remained high and in the region of 80%.

Figure 6A:
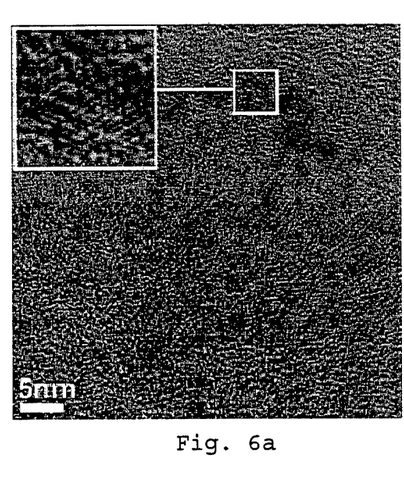
FIG. 6a is a transmission electron microscopy (TEM) image of a 'fresh' Ru/C catalyst, that is, before use.
Figure 6B:
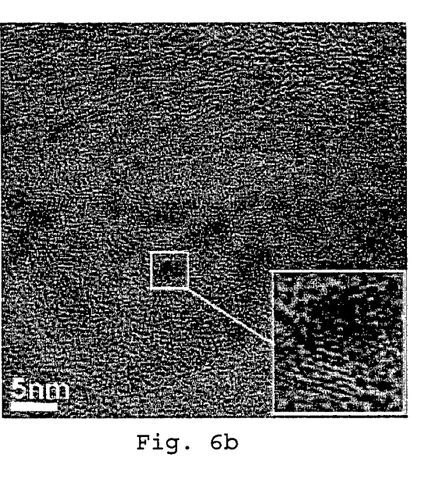
FIG. 6b is a TEM image of the Ru/C catalyst that has been used in 5 rounds of experiments. The scale bar of both figures is 5 nm.

After 5 rounds of reaction, the Ru/C catalyst was also characterized by TEM. Referring to FIG. 6a and FIG. 6b, there were no obvious changes in the morphology and particle size of the Ru nanoparticles (FIG. 6b) when compared to the fresh catalyst (FIG. 6a). This results indicated that the current reaction conditions are rather mild and that the Ru/C catalyst is stable and can be recycled under these process conditions.

Example 8

Types of Catalyst Used

Here, the effects of different types of catalyst on the synthesis of xylitol were investigated. 67.77 mg hemicellulose (0.513 mmol D-xylose unit), an equivalent amount of different types of catalyst, 4 ml water, 4 ml iso-propanol and 7 μl $H_2SO_4$ were mixed in a 10 ml Teflon-lined hydrothermal reactor and reacted at a temperature of 140° C. for 3 hours. The different types of heterogeneous catalyst investigated here were Ru/C, Pt/C, Pd/C and Raney nickel. The reactor was heated to 140° C. using a silicon oil bath or an oven and maintained at this temperature for 3 hours with magnetic stirring at 600 rpm. After the reaction, the reactor was naturally cooled down. Table 5 shows the results obtained from this example.

As shown in Table 5, when an equivalent amount of Pt/C, Pd/C and Raney nickel were used, only trace amounts of xylitol were detected. These trace amounts of xylitol are similar to that obtained without a catalyst. This suggested that Pt/C, Pd/C and Raney nickel had no catalytic activity in this reaction.

TABLE 5

Effect of different types of metal catalysts.

| Catalysts | No catalyst | Ru/C | Pd/C | Pt/C | Raney nickel |
|---|---|---|---|---|---|
| Xylitol (mg) | 1.82 | 64.8 | 1.922 | 1.816 | 2 |
| Xylitol yield | 2.33% | 83.03% | 2.46% | 2.33% | 2.56% |

Example 9

Type of Feedstock

Hemicellulose accounts for ~20 wt % of plant biomass while cellulose accounts for the rest of the plant biomass. To test whether plant biomass can be directly used as the starting material for the synthesis of xylitol, equal amounts of hemicellulose (37.5 mg) and cellulose (37.5 mg) were mixed with 25 mg Ru/C, 4 ml water, 4 ml isopropanol and 7 μl sulphuric acid. Based on the data obtained (not shown), cellulose was not affected by this reaction and remained un-reacted (100% recovered) while more than 80% of the hemicellulose was converted to xylitol. This is due largely to the more robust crystal structure of cellulose and as such, this reaction offers a means for the selective conversion of hemicellulose to xylitol, over cellulose.

Figure 7:
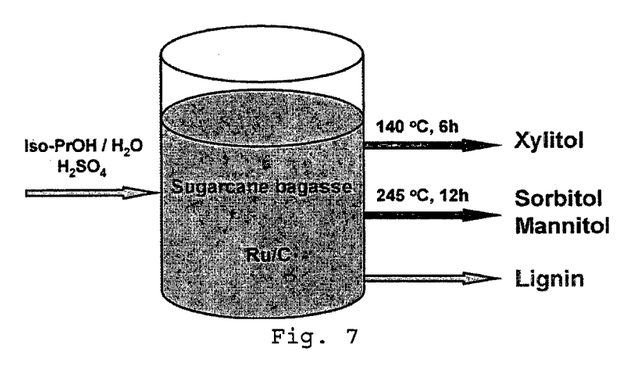
FIG. 7 is a schematic diagram showing the one-pot synthesis of sugarcane bagasse to xylitol, sorbitol and mannitol.

Another experiment was carried out using sugarcane bagasse as the feedstock. Sugarcane bagasse is an abundant waste biomass and has balanced components of both hemicellulose and cellulose (~25% hemicellulose, ~42% cellulose with lignin in the remaining percentage). Sugarcane bagasse was selected as an example of a raw material feedstock to demonstrate the one pot selective conversion process proposed in FIG. 7. Here, 75 mg of sugarcane bagasse, 25 mg Ru/C (2.4 mol %), 4 ml water, 4 ml iso-propanol and 7 μl $H_2SO_4$ were mixed in a 10 ml Teflon-lined hydrothermal reactor and reacted at a temperature of 140° C. for 3 hours. Trace amounts of xylitol was detected in the reaction system and xylose was detected as the major product. A possible reason for the minimal conversion to xylitol includes the buffering capacity of the extraneous lignin in the lignocellulosic biomass for acids, which would hinder the hydrolysis process. As such, the reaction time was subsequently doubled to 6 hours. At this stage, 15.4 mg (80.4%) xylitol (containing a small amount of arabinitol) was obtained and almost none of the xylose intermediate remained. Most importantly, there was only a negligible amount (<1%) of sorbitol/mannitol products observed in the first step of the reaction (see Table 6 below), indicating the high selectivity of the first step of the reaction towards hemicellulose. Lignin was also extracted into the isopropanol/water phase and it was precipitated as the isopropanol was removed in vacuo. 4 mL water, 4 mL isopropanol, 7 ml $H_2SO_4$ were then added to the residual solids (57.7 mg, including cellulose and solid Ru/C catalyst) and the mixture was heated to 245° C. for 12 hours, resulting in sorbitol and mannitol yields of 21.1% (see Table 6 below). Although this system is less efficient for the transformation of cellulose to the corresponding sugar alcohols, it demonstrated the excellent possibility for the one-step separation of the three main components of plant biomass by the selective conversion of hemicellulose to xylitol, with the conversion of the remaining cellulose to related sugar alcohols in one pot under mild conditions.

TABLE 6

Xylitol and hexitol yields from sugarcane bagasse

| Temperature | Reaction | Yields (%) | | |
|---|---|---|---|---|
| (° C.) | time (hours) | Xylitol[a] | Sorbitol[a] | Mannitol[a] |
| 140 | 6 | 80.4 | 0.9 | 0 |
| 245[b] | 12 | 3.1 | 19.6 | 1.5 |

[a]xylitol yield was estimated based on 18.9 mg (25.2%) of xylose from 75 mg sugarcane bagasse. Sorbitol and mannitol yield was estimated based on 31.8 mg cellulose (42.4%) in sugarcane bagasse.
[b]solid residue from first reaction carried out at 140° C. and 6 hours.

APPLICATIONS

The method may be used to synthesize a sugar alcohol or a plurality of sugar alcohols from a polysaccharide feedstock.

The method may be used to synthesize xylitol, sorbitol or mannitol and hence can be used in industries such as food, odontological and pharmaceutical industries.

The method may be used to convert plant biomass to a useful product.

The method may not require additional steps of isolating or purifying the intermediate (such as xylose) before reacting the intermediate to the final sugar alcohol. Hence, the method may be a one-step synthesis of a sugar alcohol.

The method may not require the use of high pressure hydrogen gas as the hydrogen source to reduce the intermediate to the sugar alcohol. As such, it is not necessary for sophisticated hydrogenation facilities, leading to cost savings and safety is not a major issue.

The method may lead to energy savings since the alcoholic reducing agent may be separated easily from the water solvent by evaporation. The vaporized alcoholic reducing agent can be recycled by condensing the vapor.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A method for synthesizing a sugar alcohol comprising hydrolyzing a polysaccharide in the presence of hydrogen ions ($H^+$) at a pH in the range of 2 to 3, a solvent comprising water, an alcoholic reducing agent and a hydrogen transfer catalyst to form the sugar alcohol, wherein the water and the alcoholic reducing agent are present at a volumetric ratio of 7:1 to 1:3, wherein the method comprises selecting a secondary alcohol as the alcoholic reducing agent, and wherein the hydrogen transfer catalyst is a ruthenium nanoparticles on active carbon support (Ru/C) catalyst.

2. The method as claimed in claim 1, wherein the method comprises selecting a secondary aliphatic alcohol as the alcoholic reducing agent.

3. The method as claimed in claim 1, wherein secondary alcohol has 3 to 10 carbon atoms.

4. The method as claimed in claim 3, wherein secondary alcohol is selected from the group consisting of iso-propanol, sec-butanol, 2-pentanol, 3-pentanol, 3-methyl-2-butanol, neopentanol, 2-hexanol, 3-hexanol, 2-methyl-3-pentanol, 4-methyl-2-pentanol, 3-methyl-2-pentanol, 2-heptanol, 3-heptanol, 2-octanol, 2-nanonol and 2-decanol.

5. The method as claimed in claim 1, wherein the method comprises sourcing the hydrogen ions from an acid.

6. The method as claimed in claim 5, wherein the acid excludes acids having a halide anion.

7. The method as claimed in claim 6, wherein the acid excludes acids having a chlorine anion.

8. The method as claimed in claim 5, wherein the acid is a diprotic acid.

9. The method as claimed in claim 8, wherein the acid is a sulphur oxoacid.

10. The method as claimed in claim 9, wherein the sulphur oxoacid is selected from sulphuric acid and sulphurous acid.

11. The method as claimed in claim 1, wherein the catalyst is recyclable and reusable.

12. The method as claimed in claim 1, wherein the method comprises selecting a temperature in the range of 135° C. to 155° C.

13. The method as claimed in claim 1, wherein the method comprises selecting a time period in the range of 2.5 hours to 8.5 hours.

14. The method as claimed in claim 1, wherein said sugar alcohol is selected from the group consisting of xylitol, mannitol and sorbitol.

15. The method as claimed in claim 1, wherein the polysaccharide comprises hemicellulose, cellulose or a combination thereof.

16. A method of synthesizing a plurality of sugar alcohols from a mixture of hemicellulose and cellulose, comprising:
   (a) mixing the mixture of hemicellulose and cellulose with a solvent comprising water and an alcoholic reducing agent, wherein the water and the alcoholic reducing agent are present at a volumetric ratio of 7:1 to 1:3;
   (b) hydrolyzing the hemicellulose in the presence of hydrogen ions ($H^+$) at a pH in the range of 2 to 3, water, an alcoholic reducing agent and a hydrogen transfer catalyst to form xylitol; and
   (c) hydrolyzing the cellulose in the presence of the hydrogen ions ($H^+$) at a pH in the range of 2 to 3, water, the alcoholic reducing agent and the hydrogen transfer catalyst to form at least one of sorbitol and mannitol, wherein the method comprises selecting a secondary alcohol as the alcoholic reducing agent, and wherein the hydrogen transfer catalyst is a ruthenium nanoparticles on active carbon support (Ru/C) catalyst.

17. The method as claimed in claim 16, wherein the hydrolyzing operation (a) is undertaken at a temperature of 135° C. to 155° C. for 2.5 hours to 8.5 hours.

18. The method as claimed in claim 16, wherein the hydrolyzing operation (b) is undertaken at a temperature of 240° C. to 250° C. for 11 hours to 13 hours.

19. The method as claimed in claim 1, wherein the alcoholic reducing agent is isopropanol.

20. The method as claimed in claim 16, wherein the alcoholic reducing agent is isopropanol.

\* \* \* \* \*